US008388552B2

(12) United States Patent
Effenhauser et al.

(10) Patent No.: US 8,388,552 B2
(45) Date of Patent: *Mar. 5, 2013

(54) SYSTEM FOR WITHDRAWING SMALL AMOUNTS OF BODY FLUID

(75) Inventors: Carlo Effenhauser, Weinheim (DE);
Heinz-Michael Hein, Weinheim (DE);
Karl-Heinz Koelker, Gruenstadt (DE);
Frank Deck, Niederkirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/173,510

(22) Filed: Jun. 30, 2011

(65) Prior Publication Data

US 2011/0257559 A1 Oct. 20, 2011

Related U.S. Application Data

(63) Continuation of application No. 11/858,601, filed on Sep. 20, 2007, which is a continuation of application No. 09/943,080, filed on Aug. 30, 2001, now Pat. No. 7,288,073.

(30) Foreign Application Priority Data

Jul. 20, 2001 (DE) .................. 101 34 650

(51) Int. Cl.
*A61B 5/00* (2006.01)
*B65D 81/00* (2006.01)
(52) U.S. Cl. ..................................... 600/584
(58) Field of Classification Search .......... 600/573–584; 604/264–274, 46, 157; 606/181–183; 436/180, 436/146, 148, 169, 177; 422/99–101; 137/828, 803, 833; 385/17, 18
See application file for complete search history.

(56) References Cited

U.S. PATENT DOCUMENTS

| | | |
|---|---|---|
| 2,359,550 A | 10/1944 | Eriksen |
| 3,046,987 A | 7/1962 | Ehrlich |
| 3,640,267 A | 2/1972 | Hurtig et al. |
| 3,640,388 A | 2/1972 | Ferrari |
| 3,640,393 A | 2/1972 | Hurtig |
| 3,799,742 A | 3/1974 | Coleman |
| 4,627,445 A | 12/1986 | Garcia et al. |
| 4,637,403 A | 1/1987 | Garcia et al. |
| 4,790,979 A | 12/1988 | Terminiello et al. |
| 4,837,049 A | 6/1989 | Byers et al. |
| 4,873,993 A | 10/1989 | Meserol et al. |
| 4,995,402 A | 2/1991 | Smith et al. |
| 5,014,718 A | 5/1991 | Mitchen |
| 5,029,583 A | 7/1991 | Meserol et al. |
| 5,035,704 A | 7/1991 | Lambert et al. |
| 5,054,499 A | 10/1991 | Swierczek |
| 5,192,502 A | 3/1993 | Attridge et al. |
| 5,217,480 A | 6/1993 | Haber et al. |
| 5,231,993 A | 8/1993 | Haber et al. |
| 5,284,567 A | 2/1994 | Matson |

(Continued)

FOREIGN PATENT DOCUMENTS

| | | |
|---|---|---|
| DE | 35 15 420 | 10/1986 |
| DE | 197 53 847 | 6/1999 |

(Continued)

*Primary Examiner* — Brian Szmal
(74) *Attorney, Agent, or Firm* — Woodard, Emhardt, Moriarty, McNett & Henry LLP (57) ABSTRACT

A system is provided for withdrawing small amounts of body fluid from an animal or human. The system includes a holder and a disposable lancing unit attached to the holder. The lancing unit also includes an open capillary channel for transporting the body fluid and piercing the skin.

24 Claims, 5 Drawing Sheets

U.S. PATENT DOCUMENTS

| | | | |
|---|---|---|---|
| 5,290,420 A | 3/1994 | Matson | |
| 5,514,152 A | 5/1996 | Smith | |
| 5,540,709 A | 7/1996 | Ramel | |
| 5,591,139 A | 1/1997 | Lin et al. | |
| 5,636,640 A | 6/1997 | Staehlin | |
| 5,682,233 A | 10/1997 | Brinda | |
| 5,700,695 A | 12/1997 | Yassinzadeh et al. | |
| 5,801,057 A | 9/1998 | Smart et al. | |
| 5,855,801 A | 1/1999 | Lin et al. | |
| 5,871,494 A | 2/1999 | Simons et al. | |
| 5,928,207 A | 7/1999 | Pisano et al. | |
| 5,938,679 A | 8/1999 | Freeman et al. | |
| 6,048,352 A | 4/2000 | Douglas et al. | |
| 6,051,392 A | 4/2000 | Ikeda et al. | |
| 6,099,484 A | 8/2000 | Douglas et al. | |
| 6,120,676 A | 9/2000 | Heller et al. | |
| 6,206,841 B1 | 3/2001 | Cunningham et al. | |
| 6,235,539 B1 | 5/2001 | Carpenter | |
| 6,332,871 B1 | 12/2001 | Douglas et al. | |
| 6,358,265 B1 | 3/2002 | Thorne, Jr. et al. | |
| 6,360,775 B1 | 3/2002 | Barth et al. | |
| 6,375,627 B1 | 4/2002 | Mauze et al. | |
| 6,561,989 B2 | 5/2003 | Whitson | |
| 6,572,566 B2 | 6/2003 | Effenhauser | |
| 6,592,815 B1 | 7/2003 | Zimmer | |
| 6,612,111 B1 | 9/2003 | Hodges et al. | |
| 6,783,502 B2 | 8/2004 | Orloff et al. | |
| 6,866,675 B2 | 3/2005 | Perez et al. | |
| 7,288,073 B2 * | 10/2007 | Effenhauser et al. | 600/584 |
| 7,993,284 B2 * | 8/2011 | Effenhauser et al. | 600/584 |
| 2002/0004196 A1 | 1/2002 | Whitson | |
| 2002/0103499 A1 | 8/2002 | Perez et al. | |
| 2002/0137998 A1 | 9/2002 | Smart et al. | |
| 2002/0168290 A1 | 11/2002 | Yuzhakov et al. | |
| 2002/0169470 A1 | 11/2002 | Kuhr et al. | |
| 2002/0177763 A1 | 11/2002 | Burns et al. | |
| 2003/0018282 A1 | 1/2003 | Effenhauser et al. | |
| 2003/0028087 A1 | 2/2003 | Yuzhakov et al. | |
| 2003/0028125 A1 | 2/2003 | Yuzhakov et al. | |
| 2003/0050573 A1 | 3/2003 | Kuhr et al. | |
| 2003/0144608 A1 | 7/2003 | Kojima et al. | |
| 2003/0171699 A1 | 9/2003 | Brenneman | |
| 2003/0211619 A1 | 11/2003 | Olson et al. | |
| 2003/0212344 A1 | 11/2003 | Yuzhakov et al. | |
| 2003/0212345 A1 | 11/2003 | McAllister et al. | |
| 2003/0212346 A1 | 11/2003 | Yuzhakov et al. | |
| 2003/0212347 A1 | 11/2003 | Sohrab | |
| 2003/0223906 A1 | 12/2003 | McAllister et al. | |
| 2004/0096959 A1 | 5/2004 | Stiene et al. | |
| 2004/0106941 A1 | 6/2004 | Roe et al. | |
| 2004/0127818 A1 | 7/2004 | Roe | |
| 2004/0127819 A1 | 7/2004 | Roe et al. | |
| 2004/0186394 A1 | 9/2004 | Roe et al. | |
| 2004/0193072 A1 | 9/2004 | Allen | |
| 2004/0193202 A1 | 9/2004 | Allen | |
| 2004/0236250 A1 | 11/2004 | Hodges et al. | |
| 2005/0033341 A1 | 2/2005 | Vreeke et al. | |
| 2005/0139489 A1 | 6/2005 | Davies et al. | |
| 2006/0178690 A1 | 8/2006 | Freeman et al. | |

FOREIGN PATENT DOCUMENTS

| | | |
|---|---|---|
| DE | 197 53 849 | 6/1999 |
| EP | 0 199 484 | 10/1986 |
| EP | 0 565 970 | 6/1994 |
| EP | 0 127 958 | 4/1996 |
| EP | 0 723 418 | 7/1996 |
| EP | 1 034 740 | 9/2000 |
| EP | 1 035 921 | 9/2000 |
| EP | 1 285 629 | 2/2003 |
| EP | 1 374 770 | 1/2004 |
| FR | 2 590 673 | 5/1987 |
| JP | H02-120655 | 5/1990 |
| JP | H04-194660 | 7/1992 |
| JP | H09-084781 | 9/1995 |
| JP | H09-089885 | 4/1997 |
| JP | H09-168530 | 6/1997 |
| JP | H09-285459 | 11/1997 |
| JP | H09-294737 | 11/1997 |
| WO | WO 85/04089 A1 | 9/1985 |
| WO | WO 86/00513 A1 | 1/1986 |
| WO | WO 91/06855 A1 | 5/1991 |
| WO | WO 93/09710 A1 | 5/1993 |
| WO | WO 95/10223 A2 | 4/1995 |
| WO | WO 96/00614 A1 | 1/1996 |
| WO | WO 97/42888 A1 | 11/1997 |
| WO | WO 98/35225 A1 | 8/1998 |
| WO | WO 99/30158 | 6/1999 |
| WO | WO 01/72220 A1 | 10/2001 |
| WO | WO 02/49507 A1 | 6/2002 |
| WO | WO 02/056769 A1 | 7/2002 |
| WO | WO 2004/064636 A1 | 8/2004 |

* cited by examiner

SYSTEM FOR WITHDRAWING SMALL AMOUNTS OF BODY FLUID

CROSS-REFERENCE TO RELATED APPLICATIONS

This application is a continuation of U.S. patent application Ser. No. 11/858,601, filed Sep. 20, 2007, which is a continuation of U.S. patent application Ser. No. 09/943,080, filed Aug. 30, 2001, now U.S. Pat. No. 7,288,073, which claims the benefit of German Patent Application No. 101 34 650.6, filed Jul. 20, 2001, which are hereby incorporated by reference.

BACKGROUND OF THE INVENTION

The present invention relates to the field of body fluid analyses in order to make a diagnosis or to monitor the concentration of metabolic parameters such as the blood glucose concentration.

The invention concerns a system for withdrawing small amounts of body fluid comprising a drive unit with a holding device for a disposable lancing unit which has a holding area and a capillary structure connected to the holding area. The capillary structure has at least one capillary channel and a tip for piercing the skin which faces away from the holding device. At least a part of the longitudinal extension of the capillary structure is open towards the outside.

Systems for withdrawing body fluids are already known in the prior art in which the body fluid is taken up into a disposable element. Blood collection and analytical systems are known from the document EP 0 199 484 which comprise a disposable unit with a capillary to collect body fluid and transport the body fluid into a detection area. The further development of this concept is described in WO 97/42888. The arrangement described herein is particularly suitable for collecting relatively small amounts of body fluids which is primarily accomplished by pressing a ring onto the area surrounding a collection site and a pumping movement. A system for analysis based on small amounts of interstitial fluid is known from EP 0 723 418. For this purpose a very thin closed hollow needle is inserted into the dermis and interstitial fluid is conveyed through the needle to a test zone by applying pressure to the area surrounding the puncture site. A highly miniaturized arrangement which also utilizes a closed needle to withdraw body fluid is known from U.S. Pat. No. 5,801,057. A particular advantage of this arrangement is the extremely thin needle which can be inserted at least into the arm region of a patient without essentially any pain.

Whereas the arrangement described in U.S. Pat. No. 5,801,057 already fulfils numerous practical requirements, some features are in need of improvement. A general problem with the sampling devices according to the previously mentioned document is to manufacture the hollow needle cost-effectively and as small as possible. Miniaturization which is in particular desirable with regard to minimizing the pain caused by the lancing process and minimizing the size of the puncture wound results in high manufacturing costs for the very thin closed needles and there are additional fundamental feasibility problems.

According to the present invention the requirements for systems for withdrawing small amounts of body fluids are met using needles with an open capillary structure instead of the closed needle designs known in the prior art. This not only results in considerable advantages for the manufacturing process by making it possible to manufacture the sampling system in a cost-effective and simple manner, but it also results in major advantages in the collection of body fluids since this does not only occur through the cannula tip of the hollow needle as in the case of closed needle designs but also through the open area of the capillary structure. Moreover one can also utilize the advantage that the open channel area of the needle, even when it is still inserted, is able to collect blood from the skin surface and transport it to a detection zone.

One particular field of application of systems for withdrawing small amounts of body fluid is the so-called spot-monitoring in which the concentration of particular analytes present in the body fluids is determined at a particular time. Such measurements can be carried out repeatedly at time intervals in order to monitor a change of the analyte concentration. Such an analysis using disposable test elements has proven to be particularly advantageous especially in the field of blood sugar measurement by diabetics. If excessively high blood sugar values (hyperglycaemia) occur in a diabetic over a certain period of time, this can lead to serious long-term damage such as blindness and gangrene. If, on the other hand, a diabetic falls into a state of hypoglycaemia because he has for example injected too large a dose of insulin, this can become life-threatening if the diabetic falls into a so-called hypoglycaemic shock. In contrast a regular control of the blood sugar level enables the diabetic to avoid hyperglycaemic and hypoglycaemic states and also permanently learn how to coordinate his eating habits, bodily activity and insulin medication. In addition to improving and maintaining the health of diabetics, regular blood sugar monitoring also has considerable overall economic advantages since the high costs for secondary diseases can be avoided. The reasons which prevent a more widespread and consequent use of blood sugar monitoring are primarily the pain caused by the required body fluid collection and the extensive handling steps of the common systems in the market. With the current widely used systems the diabetic or medical staff must firstly obtain a drop of blood which is usually from the finger pad. If this is to be carried out with as little pain as possible, so-called lancing devices are used. A lancing device must be firstly loaded with a lancet, tensioned, placed on the body surface and triggered. After the lancing process the user has to knead his finger in order to convey a drop of blood out of the puncture wound which should be as small as possible. Before this procedure the diabetic has to already place a test strip in a blood sugar measuring instrument and activate it. The drop of blood can now be applied to the test strip and after for example 10 seconds a blood sugar measurement is available. The user now has to also dispose of the spent lancet and test strip. The present invention enables the process of blood sugar measurement to be greatly simplified by providing a so-called integrated system in which only one (disposable) unit carries out the lancing, sampling and analytical reaction.

A system according to the invention serves to withdraw small amounts of body fluid. In this context body fluids are understood in particular as blood, interstitial fluid and mixtures of these body fluids. Whereas in conventional systems for blood collection this is usually carried out on the finger pad, the collection system according to the invention can also be used to withdraw blood from other sites on the body such as the forearm.

A disposable lancing unit for withdrawing small amounts of body fluid according to the invention has a holding area which is connected to the proximal end of an elongate capillary structure having at least one capillary channel to transport body fluid. The distal end of the capillary structure is suitable for piercing skin and at least a part of the capillary structure is open to the outside along its longitudinal extension. A capillary structure is understood within the scope of the invention as a body which transports body fluid as a result of capillary forces towards the proximal end of the capillary structure when the distal area is contacted with body fluid. With regard to this function the capillary structure according to the invention is similar to the hollow needles described in U.S. Pat. No. 5,801,057 and EP 0 723 418. However, an important difference is that at least one area which comprises at least part of the longitudinal extension of the capillary structure is open to the outside. The longitudinal extension of the capillary structure extends from the proximal end which is connected to the holding area to the distal area which is intended to be inserted into the skin. The hollow needles of the prior art only have an opening at their outermost distal end through which body fluid can enter. In contrast the capillary structure according to the invention can take up body fluid over a much larger part of its longitudinal extension. As a rule the length of the region of capillary structure which is open to the outside is more than 10% of the longitudinal dimension of the capillary structure and preferably more than 50% of the longitudinal dimension. It is particularly advantageous for the manufacturing process when the capillary structure is open to the outside along its entire longitudinal dimension.

Conventional hollow needles are manufactured in the prior art by drawing out thicker tubes. It is consequently very laborious and costly to manufacture very thin hollow needles of for example less than 0.3 mm outer diameter. In contrast U.S. Pat. No. 5,801,057 proposes a different method. A first body which has a needle area with a channel and a measuring chamber which is integrally connected to the needle is etched from silicon, the measuring chamber and channel are subsequently sealed with a layer in the area of the needle. The two bodies are for example connected by anodic bonding. The high degree of miniaturization of the blood sampling device and the bonding step in the process result in very high manufacturing costs. Furthermore, the arrangement that is formed according to the previously mentioned documents of the prior art can also only take up liquid via the tip area of the needle. According to the invention it was found that it is possible to also achieve an efficient uptake of liquid when an open capillary is present. Examples of such open capillaries are described in the following:

Open capillaries can be manufactured by photolithographic methods like those described in the document U.S. Pat. No. 5,801,057 and which are known from the field of semiconductor technology. It is also possible to provide channels, grooves etc. which are open to the outside in solid needles by milling, etching and suchlike. Such depressions lead from the tip or at least from a region adjoining the tip to the proximal end of the needle which is connected to the holding device. These depressions or capillaries do not necessarily have to run in straight lines, but can also for example be arranged in spirals, meanders etc. It is important that liquid is transported through the capillaries from the distal area of the needle into the proximal area. The cross-section of the capillaries can for example be V-shaped, semi-circular or also rectangular. It is important that a part of the cross-section is open to the outside so that fluid can penetrate into the capillary channel through the external peripheral surface of the needle.

In addition to the already mentioned methods for incorporating capillary channels into rod-shaped bodies, it is also possible to generate the capillary channels by assembling bodies. Thus it is for example possible to fasten two or more solid needles together for example by welding such that the contact areas of the solid needles form capillary channels. In a corresponding manner it is also possible to twist wires together in the form of a stranded wire such that numerous contact areas are formed which generate the capillary channels.

The capillary channels which are present in the capillary structure typically have a greater depth than width. The ratio of depth to width (generally referred to as aspect ratio) is preferably 2 to 5. The cross-section of the capillary channel is typically larger than 2500 .mu.m.sup.2 and less than 1 mm.sup.2. As already stated above it is advantageous that the capillary channels are accessible to the outside such that they can also take up body fluid while the capillary structure is inserted into tissue. In order to achieve a good uptake of body fluid the area of the capillary structure that is open to the outside should have a length of 1 mm or more.

The holding area adjoins the proximal part of the capillary structure. The holding area and capillary structure can be formed as one piece (monolithic) as well as be separate parts which are connected together by glueing, welding, press fitting or suchlike.

Monolithic structures can be generated particularly advantageously from semiconductors using the known manufacturing processes for semiconductors. This can result in a very high degree of miniaturization. In contrast the manufacturing costs may be more favourable when the lancing device is manufactured from a separate holding area and a separate capillary structure. A lancing device made of separate elements can for example be formed from a metallic capillary structure and a holding area made of plastic.

The proximal area of the capillary structure or the holding area of a lancing device according to the invention can have an evaluation zone. If the analyte concentration is for example evaluated by means of infrared spectroscopy, the detection zone does not have to contain further reagents to enable the analyte to be determined. Since the materials for the capillary structure and the holding area are usually impermeable to infrared light, analysis by reflection spectroscopy is preferred. For this purpose the evaluation zone can preferably reflect IR light which is usually the case to an adequate extent with metal surfaces. Plastics can for example be made to reflect IR light by vapour depositing or sputtering gold or aluminium. (Alternatively optically transparent windows can also be integrated).

However, in the preferred case the lancing unit has a detection zone in which a reagent is located which undergoes a detectable change on contact with an analyte to be detected in the sample of body fluid. Typical reagents for detecting glucose are based for example on glucose oxidase in conjunction with a chromogenic redox system. Reagents are well known in the prior art for an optical evaluation which form a colour with glucose from the body fluid. Furthermore reagents are also known from the field of blood sugar test strips which allow an electrochemical detection of an analyte. Since such detection systems are also well-known from the prior art they are not described in more detail herein.

The said reagent systems can be arranged in the proximal area of the capillary structure, but since there are no particularly convenient possibilities for immobilizing and evaluating the reagents in this area, it is preferable to place the reagents in the holding area. In order to wet the reagents with body fluid, the reagent either directly adjoins the capillary structure and can take up body fluid by its own capillary forces or a fluid connection (e.g. connecting channel, fleece etc.) can be provided between the capillary structure and the detection zone through which the body fluid can pass from the capillary structure into the detection zone. The lancing unit can for example be designed such that a capillary channel of the capillary structure is extended into the holding area and a reagent in the area of the holding area can be applied directly to the capillary channel which extends into this area. The reagent mixtures that are used are usually in a solid state and, due to their constituents (e.g. aluminium oxide, kieselguhr and suchlike), have such a high capillarity that they can take up body fluid from the capillary channel.

The shape of the holding area is relatively uncritical. It can for example be in the form of a small cube which has a depression to receive the reagent mixture. Special measures are usually not necessary to mount the lancing unit in a drive unit, or designs can be used that are known for disposable lancets of conventional blood sampling systems. For example the holding area can have tapers into which spring elements of a holder of the drive unit engage in order to hold the lancing unit. The lancing unit is advantageously positioned within the holder in such a manner (for example by pressing the end of the lancing unit facing away from the tip against a stop) that it allows a good control of the piercing depth of the lancing unit. Reference is made to the document EP B 0 565 970 with regard to such a holder and the interaction between the holder and the disposable lancing unit.

In a system for withdrawing small amounts of body fluids it may be advantageous to integrate a detection unit. If a lancing unit containing a reagent is used which changes colour or forms a colour when an analyte is present, the system can have an optical detection unit comprising a light source and a detector to detect transmitted or reflected light. If electrochemical detection is used, the system can have electrodes which contact the reagent of the lancing unit or the contacts of the lancing unit which in turn contact the reagent. For the evaluation the system can have the electronic devices known in the prior art in order to determine the concentration of the analyte for example by measuring the so-called Cotrell current. If it is intended to carry out a reagent-free analysis, the system can for example comprise an infrared radiation source and an infrared detector and devices for the spectral resolution of the radiation reflected from the evaluation zone.

The collection system according to the invention additionally has a drive unit which, when activated, moves the holder from a first into a second position such that the lancing unit performs a lancing movement. Such drive units are well-known from the field of blood sampling systems. It can for example contain a spring which is tensioned by the user and drives the lancing unit when it relaxes. A particularly advantageous drive unit is described in EP B 0 565 970.

With the lancing unit according to the invention or the collection system according to the invention, body fluid can be withdrawn while the capillary structure or a part thereof is inserted into the skin (i.e. withdrawal directly from the body or from body fluid emerging from the body on the body surface) or the capillary structure can be retracted from the body after the piercing operation and take up body fluid that emerges from the body surface. A withdrawal in which the capillary structure remains in the body to collect body fluid is especially suitable for sampling from the arm. This is due to the fact that small incisions on the arm close again very rapidly such that no fluid or only very small amounts of fluid emerge after the piercing. On the other hand the sensitivity to pain is much less pronounced on the arm as compared for example to the finger and thus when the capillary structure remains in the body this is not felt to be painful. As described above an advantage of a capillary structure that is open to the outside compared to conventional hollow needles is that fluid can be taken up through the open area whereas the area for taking up liquids by hollow needles is limited to the front end of the needle. The latter is particularly disadvantageous when the needle opening becomes sealed by tissue components during the piercing process such that no liquid or only an inadequate amount can be taken up.

It also has an advantage over conventional hollow needles in the case of a withdrawal in which the capillary structure is retracted from the tissue after the lancing process. As already described capillary structures that are open to the outside can be much more simply and cheaply manufactured than closed hollow needles.

Furthermore a withdrawal process can be carried out with the lancing units according to the invention which is a combination of the previously mentioned processes. In this combination process piercing is firstly carried out, the capillary structure is pulled back over a part of the piercing path and is allowed to reside there for a collection period of several seconds. An advantage of this process is that the retraction of the capillary structure exposes part of the lancing channel such that body fluid can collect in it and can enter from there into the capillary structure.

A further decisive factor which is important for an efficient uptake of body fluid by means of the capillary structure is the wettability of the capillary channels. If capillary structures made of silicon are used, these are usually adequately wettable due to a silicon oxide layer on the surface. If metals are used for the capillary structure, these are often relatively difficult to wet. This can be counteracted by a number of different measures such as silication of the surface. The wettability is usually adequate when the liquid in the capillaries has a concave meniscus which is synonymous with a wetting angle of less than 90°.

BRIEF DESCRIPTION OF THE DRAWINGS

The invention is illustrated in more detail on the basis of figures.

DETAILED DESCRIPTION OF PREFERRED EMBODIMENTS OF THE INVENTION

Figure 1:
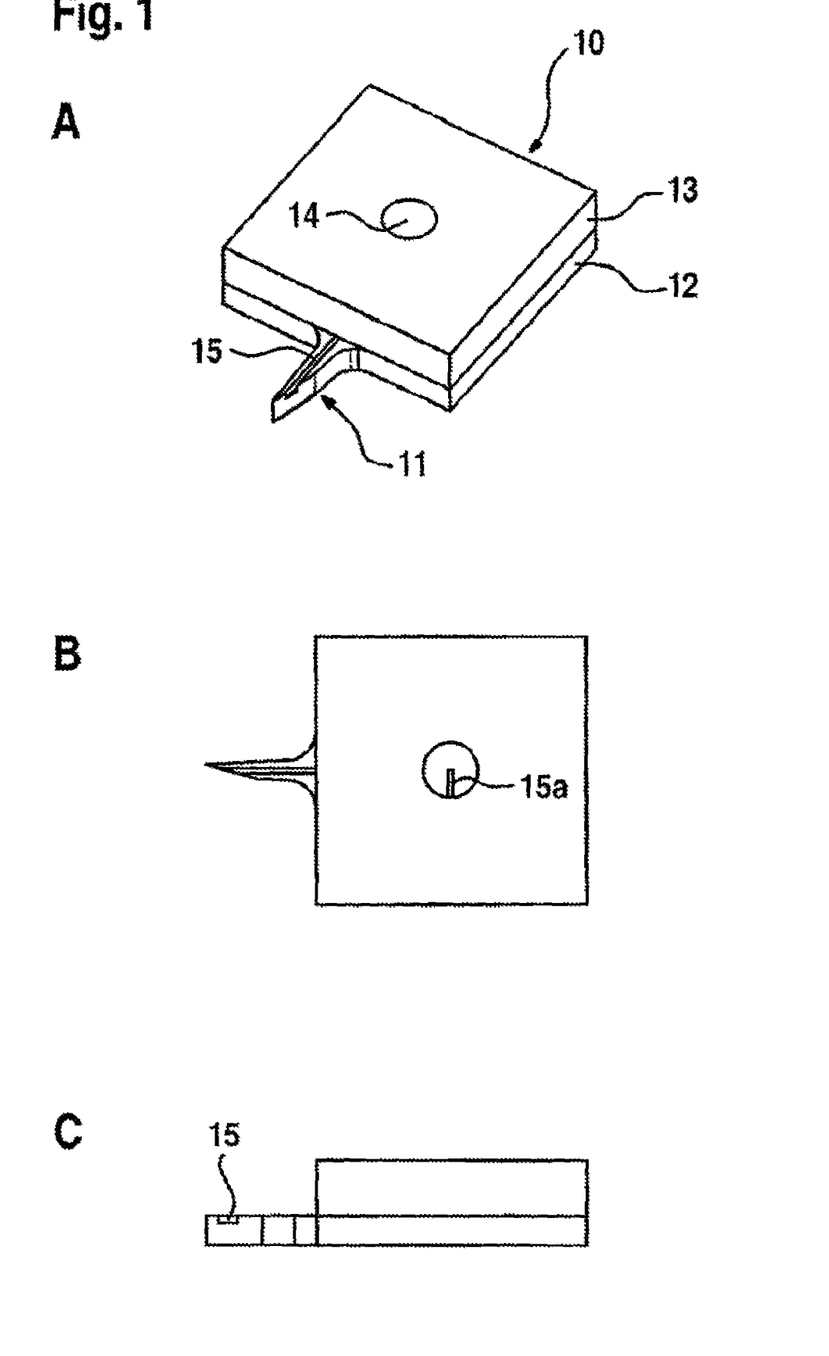
FIG. 1: Disposable lancing unit made of silicon.

FIG. 1 shows a disposable lancing device in three views. The perspective view in FIG. 1A shows that the lancing unit 10 has a capillary structure 11 which is arranged in a holding area 12. The holding area 12 is capped with a plate 13 which has a window 14. The capillary structure 11 is designed such that its distal end has a tip in order to pierce the skin. In addition a capillary channel 15 which is open at the top is arranged in the capillary structure. This capillary channel extends further inside the lancing unit and reaches a detection zone which is arranged below the window 14. The end 15A of the capillary channel can be seen in the window region in FIG. 1B. In this case the end is visible since there is no test chemistry arranged above the channel. However, in the ready-to-use state a detection area e.g. an optical detection system for glucose is arranged above this end.

FIG. 1C shows a side view of the lancing unit which shows that the side of the capillary channel 15 is open towards the top as well as at the distal end of the capillary structure. The length of the capillary structure shown is 1.6 mm and the width and depth of the capillary channel 15 are 50 and 150 μm respectively. In another example, the length of the capillary structure is in the range from 0.3 to 3 mm and the cross-section of the capillary structure is in the range from 0.03 to 0.8 mm.

Figure 2:
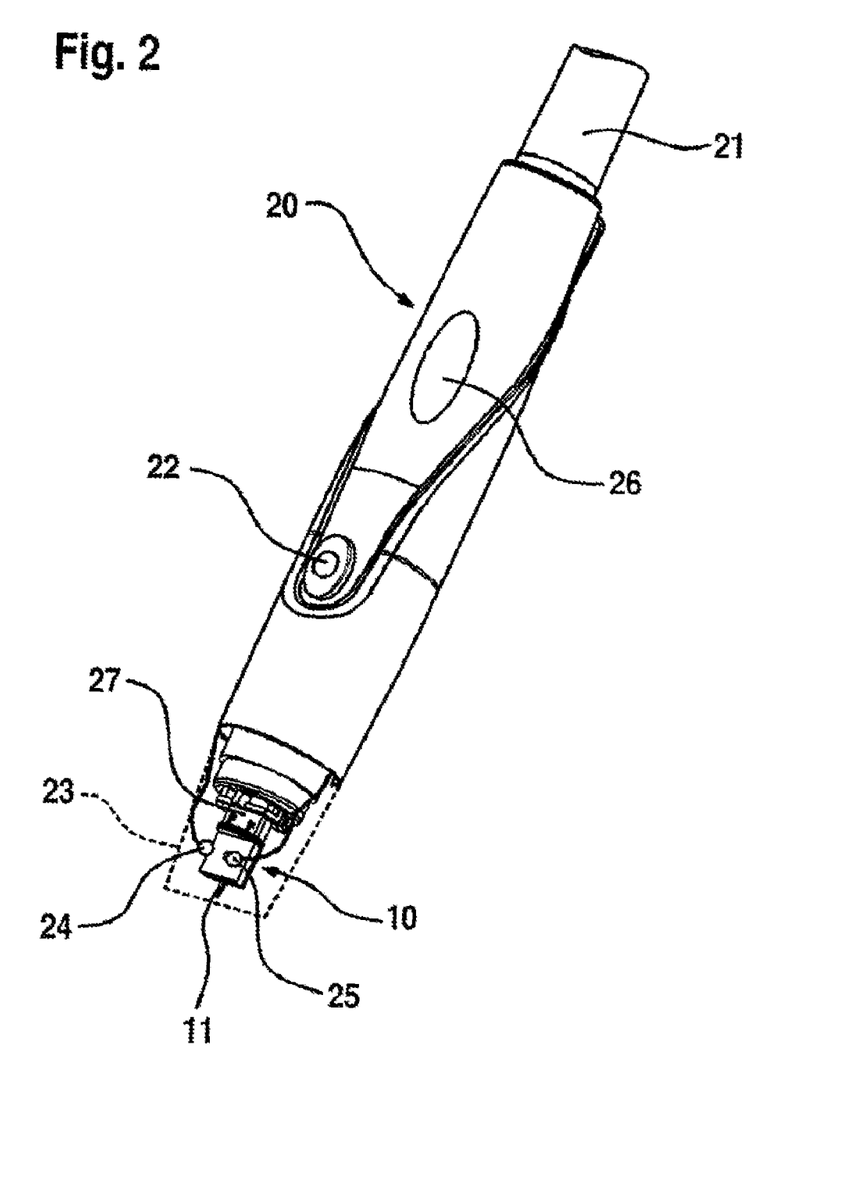
FIG. 2: System for withdrawing body fluid comprising the lancing unit from FIG. 1, a drive unit and an optical evaluation device.

FIG. 2 shows a system (20) for withdrawing body fluid which comprises a lancing device as shown in FIG. 1, a drive unit and an optical evaluation device. The figure shows a system which is based on a blood collection device according to EP 1034740. The lancing device of FIG. 1 is located in the holder of the blood collection device in which a disposable lancet is arranged in previous systems. The drive mechanism is tensioned by actuating the push-button 21 and the lancing process, i.e. the movement of the lancing device, is triggered by operating the release button 22. In this process the capillary area 11 emerges from an exit port (not shown) in the cap 23 (shows by the dashed line) and punctures the skin which is located at the cap opening in order to collect blood. In contrast to blood lancing devices which are commercially available under the name Softclix Pro, the capillary region is not pulled back behind the cap opening but remains over its maximum piercing depth in the tissue or is partially retracted such that emerging body fluid can be taken up into the capillary. As shown in conjunction with FIG. 1 body fluid passes through the capillaries into an evaluation area in which it is possible to determine an analyte. FIG. 2 shows an optical evaluation system which comprises a light source 24 and a photodetector 25. The evaluation area is illuminated by the light source 24 (e.g. a light emitting diode) through the window 14 and radiation reflected from the evaluation area is captured by the photodetector 25. An analyte concentration is determined by an evaluation unit (not shown) in the system from the intensity received by the photodetector and displayed on the display 26. After the measurement is completed the user can remove the system 20 from the body surface, remove the cap 23 and eject the lancing unit 10. A new lancing unit can be inserted into the holder 27 of the system, e.g. from a magazine, for a further measurement.

Figure 3:
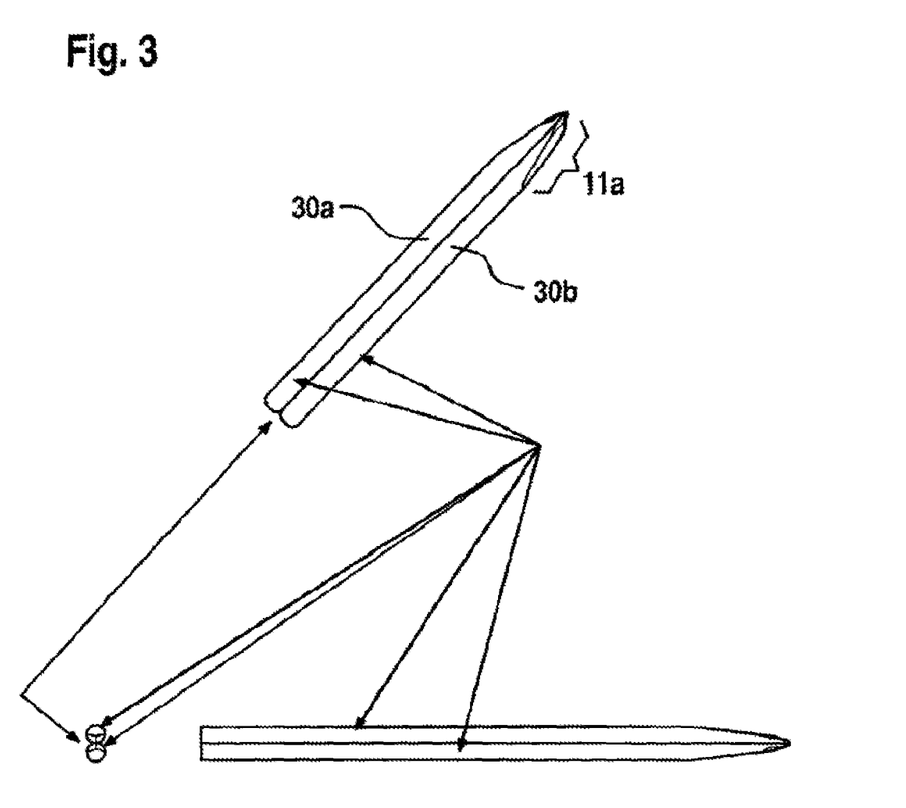
FIG. 3: Capillary region of a disposable lancing unit composed of 2 solid needles that are welded together.

FIG. 3 shows the generation of a capillary structure by welding two solid needles. FIG. 3 shows that two opposing capillary channels are formed which are open to the outside by welding two cylindrical metal wires. One end of the structure that is obtained is ground to form a tip which enables it to pierce the skin. In the example shown metal wires made of medical stainless steel with a cross-section of 400 μm are used. The tip area 11a of the capillary structure has a length of about 2 mm. The two wires are welded by passing a current through the two wires, one wire being connected as the anode and the other as the cathode.

Figure 4:
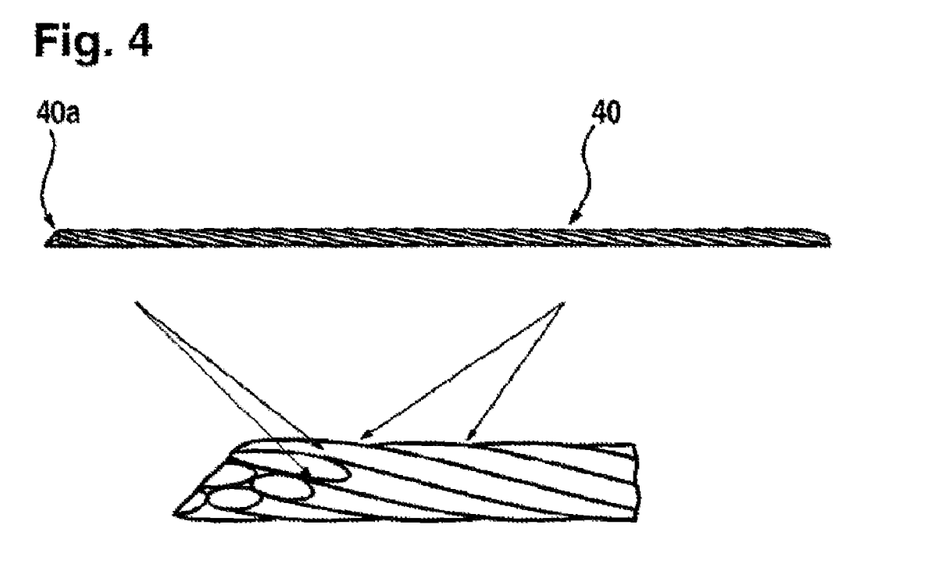
FIG. 4: Capillary structure formed from wires that are twisted together (stranded wire structure).

FIG. 4 shows a capillary structure in the form of a stranded wire. In order to generate this stranded structure 40, metal wires having a diameter of 20 to 70 μm were twisted together and one end was cut at an oblique angle to result in a tip area 40a which can pierce the skin. The enlargement in FIG. 4 shows the tip region of the open capillary channels (indicated by arrows) which are formed by the adjacent wires.

Figure 5:
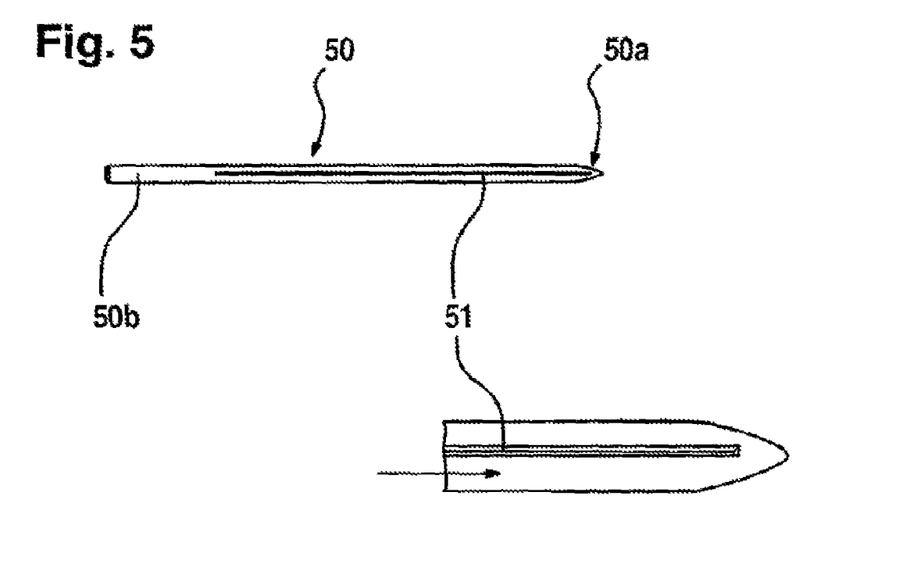
FIG. 5: Capillary structure in the form of a solid needle on the surface of which capillary channels are located.

FIG. 5 shows a capillary structure 50 which has been generated from a solid needle. The needle has a proximal area 50b which can be held in a holding area. The tip area 50A of the needle is bevelled like conventional blood lancets in order to allow a largely painless skin penetration. The capillary channel 51 which is open to the outside was milled into the solid needle. A cross-section of this capillary channel is about 60×150 μm.

Figure 6:
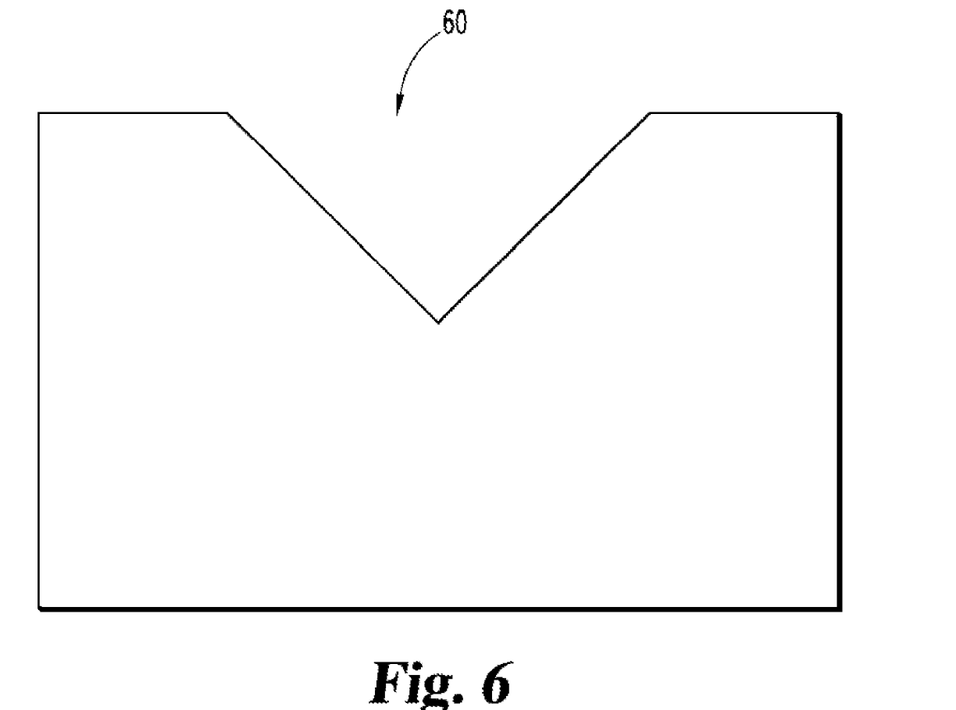
FIG. 6: Cross section of a capillary having a V-shaped configuration.

FIG. 6 shows a cross section of a capillary 60 that is V-shaped. Although the present invention has been described in connection with preferred embodiments thereof, it will be appreciated by those skilled in the art that additions, modifications, substitutions and deletions not specifically described may be made without departing from the spirit and scope of the invention as defined in the appended claims.

What is claimed is:

1. System for withdrawing small amounts of body fluid, comprising:
    a drive unit comprising a holder, the drive unit is configured to move the holder from a first position into a second position when the drive unit is activated;
    a disposable lancing unit having an elongate capillary structure and a needle with a distal end for piercing skin, the capillary structure having a longitudinal extension with at least one capillary channel for transporting body fluid, wherein the at least one capillary structure is open to the outside from at least the distal end to at least an upper end of the needle that is above the skin during piercing so that the capillary channel is vented when the body fluid is drawn into the capillary channel; and
    wherein the holder of the drive unit is configured to hold the distal end of the needle below the skin and the upper end of the needle above skin to draw body fluid from both the surface of the skin and below the surface of the skin.

2. System as claimed in claim 1, in which the disposable lancing unit has a holding area.

3. System as claimed in claim 2, in which the holding area has a detection zone for detecting one or several analytes, the detection zone being arranged for taking up the body fluid from the capillary structure.

4. System as claimed in claim 2, in which the capillary structure and holding area are integrally connected together.

5. System as claimed in claim 4, in which the holding area and capillary structure are integrally manufactured from a single piece of material.

6. System as claimed in claim 2, in which the holding area and capillary structure are manufactured from a semiconductor.

7. System as claimed in claim 1, in which the drive unit is configured to move the disposable lancing unit in such a manner that the disposable lancing unit remains in the second position for a collection time period and, subsequently, move the disposable lancing unit into a position in which the distal end of the capillary structure is outside the skin.

8. System as claimed in claim 1, in which the drive unit is configured to move the disposable lancing unit in such a manner that after reaching the second position the disposable lancing unit is moved back into a collecting position in which a section of the capillary structure located in the skin is shorter than in the second position.

9. System as claimed in claim 1, in which the area of the capillary structure that is open to the outside has a channel shape.

10. System as claimed in claim 9, in which the channel-shaped area has a V-shaped cross-section.

11. System as claimed in claim 1, in which the length of the capillary structure is in the range from 0.3 to 3 mm and the cross-section of the capillary structure is in the range from 0.03 to 0.8 mm.

12. A system, comprising:
    a disposable lancing unit including
        a lancing tip with a sharpened end configured to pierce a surface of skin,
        a detection zone containing a reagent configured to detect analyte in body fluid from the skin, and a capillary groove in the disposable lancing unit extending uncovered along at least a length of the lancing tip, wherein the capillary groove has adequate wettability to transport the body fluid via capillary action to the detection zone;

a drive mechanism configured to actuate the disposable lancing unit to pierce the surface of the skin, the drive mechanism being configured to hold the disposable lancing unit at an extended position where the capillary groove extends from below the surface of the skin to above the surface of the skin to promote venting during uptake of the body fluid; and wherein the capillary groove is configured to collect the body fluid below and above the surface of the skin.

13. The system of claim 12, wherein:
the capillary groove has an aspect ratio from 2 to 5; and
the capillary groove has a wetting angle of less than 90°.

14. The system of claim 12, wherein the drive mechanism is configured to partially retract the lancing unit in the skin so that the capillary groove remains in part in the skin to promote pooling of the body fluid.

15. A method, comprising:
piercing skin with a lancing unit by actuating a drive unit;
collecting body fluid with an uncovered capillary groove of the lancing unit, wherein said collecting the body fluid includes venting the capillary groove by positioning the lancing unit with the drive unit so that the capillary groove extends from below the surface of the skin to above the surface of the skin; and
transporting the body fluid in the open capillary groove via capillary action to a detection zone of the lancing unit, wherein said transporting the body fluid includes drawing the body fluid solely via the capillary action.

16. The method of claim 15, further comprising:
said collecting the body fluid includes allowing the capillary groove to reside within the incision in the skin for a collection period.

17. The method of claim 15, further comprising:
retracting partially the lancing unit in the incision so that the capillary groove remains in part in the incision to promote pooling of the body fluid in the incision.

18. The method of claim 15, wherein the lancing unit remains at a maximum penetration depth into the skin during said collecting.

19. The method of claim 15, further comprising:
detecting analyte in the body fluid in the detection zone.

20. A method, comprising:
piercing skin with a lancing unit by actuating a drive unit;
collecting body fluid with an uncovered capillary groove of the lancing unit, wherein said collecting the body fluid includes venting the capillary groove by positioning the lancing unit with the drive unit so that the capillary groove extends from below the surface of the skin to above the surface of the skin;
transporting the body fluid in the open capillary groove via capillary action to a detection zone of the lancing unit; and
wherein the body fluid is drawn from both the surface of the skin and below the surface of the skin during said collecting.

21. The method of claim 20, further comprising:
said collecting the body fluid includes allowing the capillary groove to reside within the incision in the skin for a collection period.

22. The method of claim 20, further comprising:
retracting partially the lancing unit in the incision so that the capillary groove remains in part in the incision to promote pooling of the body fluid in the incision.

23. The method of claim 20, wherein the lancing unit remains at a maximum penetration depth into the skin during said collecting.

24. The method of claim 20, further comprising:
detecting analyte in the body fluid in the detection zone.

* * * * *